United States Patent
Takabatake et al.

(10) Patent No.: US 10,518,033 B2
(45) Date of Patent: Dec. 31, 2019

(54) PHARMACEUTICAL CARTRIDGE HOLDING UNIT, AND PHARMACEUTICAL INJECTION DEVICE PROVIDED THEREWITH

(71) Applicants: PHC Corporation, Toon-shi, Ehime (JP); JCR PHARMACEUTICALS CO., LTD., Ashiya-shi, Hyogo (JP)

(72) Inventors: Yukihiro Takabatake, Ehime (JP); Toshiaki Iio, Ehime (JP); Seiji Kikuchi, Ehime (JP); Yutaro Fujino, Ehime (JP); Takashi Hanada, Hyogo (JP)

(73) Assignee: PHC CORPORATION, Ehime (JP)

( * ) Notice: Subject to any disclaimer, the term of this patent is extended or adjusted under 35 U.S.C. 154(b) by 31 days.

(21) Appl. No.: 15/502,779

(22) PCT Filed: Sep. 9, 2015

(86) PCT No.: PCT/JP2015/075633
§ 371 (c)(1),
(2) Date: Feb. 8, 2017

(87) PCT Pub. No.: WO2016/052117
PCT Pub. Date: Apr. 7, 2016

(65) Prior Publication Data
US 2017/0224921 A1    Aug. 10, 2017

(30) Foreign Application Priority Data

Sep. 30, 2014 (JP) .................................. 2014-199832

(51) Int. Cl.
*A61M 5/00* (2006.01)
*A61M 5/24* (2006.01)
(Continued)

(52) U.S. Cl.
CPC ............ *A61M 5/2422* (2013.01); *A61M 5/20* (2013.01); *A61M 5/24* (2013.01); *A61M 5/28* (2013.01);
(Continued)

(58) Field of Classification Search
CPC ........ A61M 5/24; A61M 5/2422; A61M 5/28; A61M 5/31511; A61M 5/31576;
(Continued)

(56) References Cited

U.S. PATENT DOCUMENTS 5,092,842 A * 3/1992 Bechtold ................. A61M 5/20
604/135
6,544,234 B1   4/2003 Gabriel
(Continued)

FOREIGN PATENT DOCUMENTS

EP    2253348 A1    11/2010
EP    2357013 A1    8/2011
(Continued)

OTHER PUBLICATIONS

Search Report from the corresponding European Patent Application No. 15845876.0 dated Oct. 5, 2017.
(Continued)

*Primary Examiner* — Rebecca E Eisenberg
(74) *Attorney, Agent, or Firm* — Wenderoth, Lind & Ponack, L.L.P.

(57) ABSTRACT

A pharmaceutical cartridge holding unit holds a pharmaceutical cartridge and is mounted to a pharmaceutical injection device main body in order to mount the pharmaceutical cartridge to a pharmaceutical injection device. The pharmaceutical cartridge holding unit comprises an outer peripheral cap having a front end side opening and a rear end side opening, and a cartridge cover that is on an inside of the outer peripheral cap and is held in a state of being able to (Continued)

slide forward and backward with respect to the outer peripheral cap. The outer peripheral cap has a guide component configured to guide sliding of the cartridge cover forward and backward, a stopper configured to prevent the cartridge cover from coming loose from the outer peripheral cap, and an engagement component that can engage with the pharmaceutical injection device main body.

6 Claims, 11 Drawing Sheets (51) Int. Cl.
    *A61M 5/20*         (2006.01)
    *A61M 5/28*         (2006.01)
    *A61M 5/315*       (2006.01)

(52) U.S. Cl.
    CPC .... *A61M 5/31511* (2013.01); *A61M 5/31576* (2013.01); *A61M 2005/206* (2013.01); *A61M 2005/2407* (2013.01); *A61M 2005/2488* (2013.01); *A61M 2005/31588* (2013.01); *A61M 2205/10* (2013.01); *A61M 2205/3306* (2013.01)

(58) Field of Classification Search
    CPC .... A61M 2005/206; A61M 2005/2407; A61M 2005/2488; A61M 2005/31588; A61M 2205/10; A61M 5/20
    See application file for complete search history.

(56) References Cited

U.S. PATENT DOCUMENTS

| | | |
|---|---|---|
| 8,398,602 B2 | 3/2013 | Iio et al. |
| 8,674,656 B2 | 3/2014 | Iio et al. |
| 2005/0197650 A1 | 9/2005 | Sugimoto et al. |
| 2007/0078408 A1 | 4/2007 | Wang |
| 2009/0043265 A1 | 2/2009 | Schneider |
| 2010/0292643 A1 | 11/2010 | Wilmot et al. |
| 2011/0004165 A1 | 1/2011 | Iio et al. |
| 2011/0218502 A1 | 9/2011 | Iio et al. |
| 2013/0172819 A1 | 7/2013 | Iio et al. |
| 2013/0175192 A1 | 7/2013 | Iio et al. |
| 2013/0274677 A1 | 10/2013 | Ekman et al. |
| 2014/0207106 A1 | 7/2014 | Bechmann et al. |
| 2014/0330215 A1 | 11/2014 | Kikuchi et al. |

FOREIGN PATENT DOCUMENTS

| | | |
|---|---|---|
| JP | H02-502971 A | 9/1990 |
| JP | 2005-245852 A | 9/2005 |
| JP | 2007-111301 A | 5/2007 |
| JP | 2010-035925 A | 2/2010 |
| JP | 2014-502888 A | 2/2014 |
| JP | 2014-111173 A | 6/2014 |
| JP | 2014-526297 A | 10/2014 |
| WO | 00/41754 A1 | 7/2000 |
| WO | 2009/125582 A1 | 10/2009 |
| WO | 2010/000559 A1 | 1/2010 |
| WO | 2012/064258 A1 | 5/2012 |
| WO | 2012/066767 A1 | 5/2012 |
| WO | 2013/084505 A1 | 6/2013 |
| WO | 2014/049924 A1 | 4/2014 |

OTHER PUBLICATIONS

Search Report from the relevant European Patent Application No. 15847515.2 dated Oct. 17, 2017.
Office Action from the corresponding Japanese Patent Application No. 2016-551971 dated Jan. 9, 2018.
International Search Report of Int'l Appln. No. PCT/JP2015/075633 dated Oct. 20, 2015.
International Search Report of Int'l Appln. No. PCT/JP2015/077104 dated Dec. 15, 2015.
Office Action dated Oct. 21, 2019 in U.S. Appl. No. 15/504,008.

\* cited by examiner

PHARMACEUTICAL CARTRIDGE HOLDING UNIT, AND PHARMACEUTICAL INJECTION DEVICE PROVIDED THEREWITH

PRIORITY

This is a National Stage Application under 35 U.S.C. § 365 of International Application PCT/JP2015/075633, with an international filing date of Sep. 9, 2015, which claims priority to Japanese Patent Application No. 2014-199832 filed on Sep. 30, 2014. The entire disclosures of International Application PCT/JP2015/075633 and Japanese Patent Application No. 2014-199832 are hereby incorporated herein by reference.

TECHNICAL FIELD

Certain implementations of the present invention relate to a pharmaceutical cartridge holding unit and to a pharmaceutical injection device provided with this unit.

BACKGROUND

A pharmaceutical cartridge holding a growth hormone pharmaceutical, for example, is mounted to a pharmaceutical injection device main body in a state of being mounted to a cartridge cover, and then an outer peripheral cap is mounted around the outside of the cartridge cover. After this, the pharmaceutical inside the pharmaceutical cartridge is injected into the body by a pharmaceutical injection device.

After this pharmaceutical injection, first the outer peripheral cap is removed from the pharmaceutical injection device main body, and then the cartridge is removed from the pharmaceutical injection device main body, and the pharmaceutical cartridge is removed from the cartridge cover, after which the pharmaceutical cartridge is stored in a cool place such as a refrigerator

SUMMARY

With certain pharmaceutical cartridges, when a pharmaceutical is to be injected, the user first has to mount the pharmaceutical cartridge inside of the cartridge cover, then mount the cartridge cover (to which the pharmaceutical cartridge has been mounted) to the pharmaceutical injection device main body, and then mount the outer peripheral cap around the outside of the cartridge cover, and only then is able to inject the pharmaceutical.

That is, to perform pharmaceutical injection using a pharmaceutical cartridge that has been stored in a cool place, the above-mentioned work is required every time (mounting the pharmaceutical cartridge inside the cartridge cover, then mounting the cartridge cover to which this pharmaceutical cartridge has been mounted to the pharmaceutical injection device main body, and then mounting the outer peripheral cap around the outside of the cartridge cover), which means that considerable work is entailed.

Also, after this pharmaceutical injection, the worker has to remove the pharmaceutical cartridge and store it in a cool place, and once again he must remove the outer peripheral cap from the pharmaceutical injection device main body, then remove the cartridge cover from the pharmaceutical injection device main body, and then remove the pharmaceutical cartridge from the cartridge cover, and store the pharmaceutical cartridge in a cool place such as refrigerator, so a very large amount of work is entailed.

In view of this, and in light of the problems encountered with the above prior art, it is an object of certain implementations of the present invention to provide a pharmaceutical cartridge holding unit that entails less work in the mounting or storing of the pharmaceutical cartridge, as well as a pharmaceutical injection device equipped with this unit.

To achieve this object, certain implementations of the pharmaceutical cartridge holding unit of the present invention is a pharmaceutical cartridge holding unit which holds a pharmaceutical-filled cartridge and is mounted to a pharmaceutical injection device main body, in order to mount the pharmaceutical-filled cartridge to a pharmaceutical injection device, said unit comprising peripheral cap having openings on the front end side and the rear end side, and a cartridge cover that is disposed on the inside of the outer peripheral cap and is held in a state of being able to slide forward and backward with respect to the outer peripheral cap, wherein the outer peripheral cap has a guide component that guides the sliding of the cartridge cover forward and backward, a stopper that prevents the cartridge cover from coming loose from the outer peripheral cap, and a first engagement component that can engage with the pharmaceutical injection device main body. The above configuration achieves the stated object.

Specifically, with certain implementations of the present invention, the unit can be handled in a state in which the cartridge cover is placed inside the outer peripheral cap, so when the pharmaceutical cartridge is stored in a cool place, the pharmaceutical cartridge can be stored along with the cartridge cover and the outer peripheral cap. Also, after store, when a pharmaceutical is to be injected, these components can be mounted as a unit to the pharmaceutical injection device, which means that far less work is entailed.

Certain implementations provide a pharmaceutical cartridge holding unit that entails less work in the mounting and storing of the pharmaceutical cartridge, as well as a pharmaceutical injection device equipped with this unit.

DETAILED DESCRIPTION

Embodiments of the present invention will now be described in detail through reference to the drawings.

1. Overview of Pharmaceutical Injection Device

Figure 1:
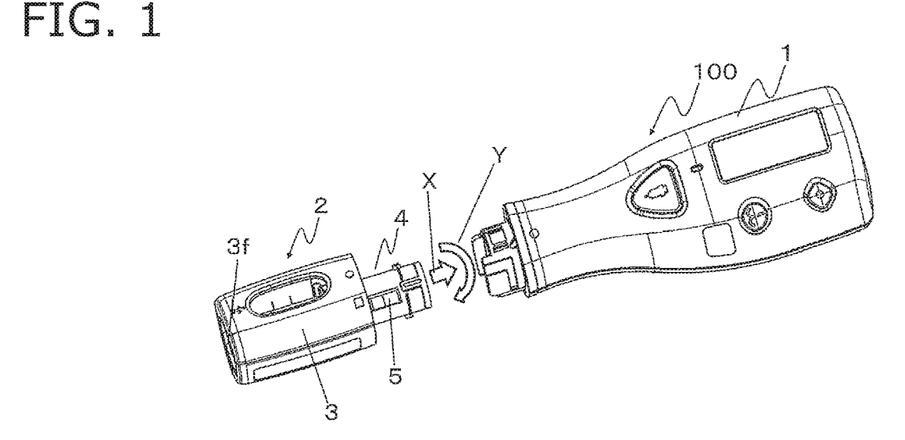
FIG. 1 is an oblique view of the state when a pharmaceutical cartridge holding unit is to be mounted to a pharmaceutical injection device in an embodiment of the present invention.
Figure 2:
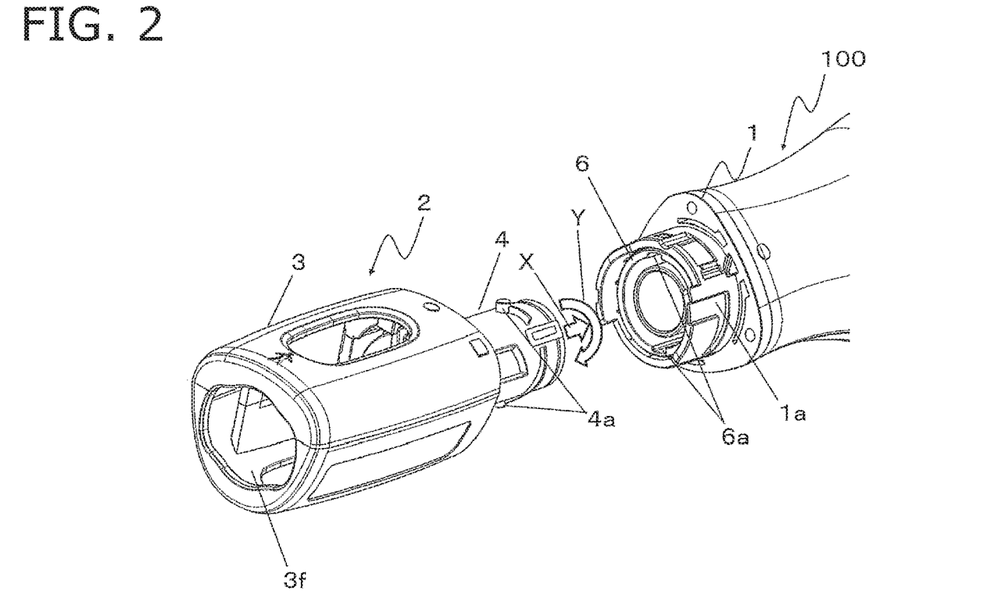
FIG. 2 is an oblique view of the state when the pharmaceutical cartridge holding unit is to be mounted to the pharmaceutical injection device in FIG. 1.

FIGS. 1 and 2 are oblique views of the state when a pharmaceutical cartridge holding unit is to be mounted to a pharmaceutical injection device.

As shown in FIGS. 1 and 2, the pharmaceutical injection device in this embodiment comprises a pharmaceutical injection device main body 100 and a pharmaceutical cartridge holding unit 2.

The pharmaceutical cartridge holding unit 2 is configured so as to be removably mounted on the distal end side (also called the front end side) of a main body case 1 of the pharmaceutical injection device main body 100.

More specifically, the pharmaceutical cartridge holding unit 2 comprises an outer peripheral cap 3 having openings at both ends, and a cylindrical cartridge cover 4 that is disposed in the interior of the outer peripheral cap 3. The openings at both ends of the pharmaceutical cartridge holding unit 2 are the distal end opening 3f shown in FIG. 2, and the rear end opening 3e shown in FIG. 7B (discussed below).

The outer peripheral cap 3 also serves to restrict the injection position and the injection depth when its distal end opening 3f side comes into contact with the skin during injection of a pharmaceutical into the body.

The cartridge cover 4 attached in the interior of the outer peripheral cap 3 will be described in detail below through reference to FIG. 9, etc., but it is similar to the outer peripheral cap 3 in that it has openings at both ends, and is configured to hold in its interior a pharmaceutical cartridge 5 filled with a pharmaceutical.

In this Specification, the distal end opening 3f side will be called the front side or distal end side of the pharmaceutical cartridge holding unit 2 and the pharmaceutical injection device, and the opposite side thereof (the X direction side in FIG. 1) will be called the rear side.

2. Mounting Between Pharmaceutical Cartridge Holding Unit and Main Body Case

The portion where the pharmaceutical cartridge holding unit 2 is mounted to the main body case 1 will now be described.

As shown in FIG. 2, the cartridge cover 4 constituting the pharmaceutical cartridge holding unit 2 is provided with protrusions 4a that engage with grooves 6a in an inner case 6 disposed in the interior of the main body case 1. In FIG. 2, an example is shown in which two each of the protrusions 4a and the grooves 6a are provided and they are disposed at positions that are separated by 180°, but the number of each is not limited to two, and may instead be one, or three or more.

Consequently, when the pharmaceutical cartridge holding unit 2 is mounted to the main body case 1, the protrusions 4a of the cartridge cover 4 are guided by the grooves 6a of the inner case 6 in the direction indicated by the arrow X (parallel to the axis of the cylindrical cartridge cover 4, and facing the main body case 1), and when the pharmaceutical cartridge holding unit 2 is then turned in the direction indicated by the arrow Y (turned to the right (clockwise) around the axis of the above-mentioned arrow X), the protrusions 4a go all the way down into the grooves 6a. The cartridge cover 4 is thus mounted to the inner case 6.

The protrusions 4a of the cartridge cover 4 here correspond to an example of a second engagement component, and the grooves 6a of the inner case 6 correspond to an example of a second engaged part.

At the same time as the above, the outer peripheral cap 3 is mounted to the main body case 1.

That is, just as with the protrusions 4a above, protrusions 3b (see FIG. 7B), which are an example of a first engagement component, are provided on the inner peripheral side of the outer peripheral cap 3 constituting the pharmaceutical cartridge holding unit 2, and main body grooves 1a (see FIG. 2) are provided to the main body case 1 so as to engage with the protrusions 3b of the outer peripheral cap 3.

The grooves 6a here are formed in an L shape so as to guide the protrusions 4a in the axial direction and the rotation direction. The main body grooves 1a are formed in an L shape so as to guide the protrusions 3b (see FIG. 7B), which are formed on the inner peripheral side of the outer peripheral cap 3, in the axial direction and the rotation direction. The phases of the protrusions 4a and the grooves 6a, and of the protrusions 3b and the main body grooves 1a are matched (it could also be said that the positional relations are matched) so that the protrusions 3b (see FIG. 7B) formed on the inner peripheral side of the outer peripheral cap 3 and the main body grooves 1a (see FIG. 2) will coincide when the protrusions 4a are inserted into the grooves 6a. So the outer peripheral cap 3 is mounted to the main body case 1, and the cartridge cover 4 is mounted to the inner case 6, by operating in the above-mentioned X and Y directions. The inner case 6 is disposed in the interior of the main body case 1, and is able to slide with respect to the main body case 1. When the pharmaceutical cartridge holding unit 2 is mounted to the main body case 1, the cartridge cover 4 is able to slide along with the inner case 6.

3. Internal Configuration and Pharmaceutical Injection Operation of Pharmaceutical Injection Device Main Body FIG. 18 is a simplified cross section of the internal configuration of the pharmaceutical injection device in this embodiment.

Figure 18:
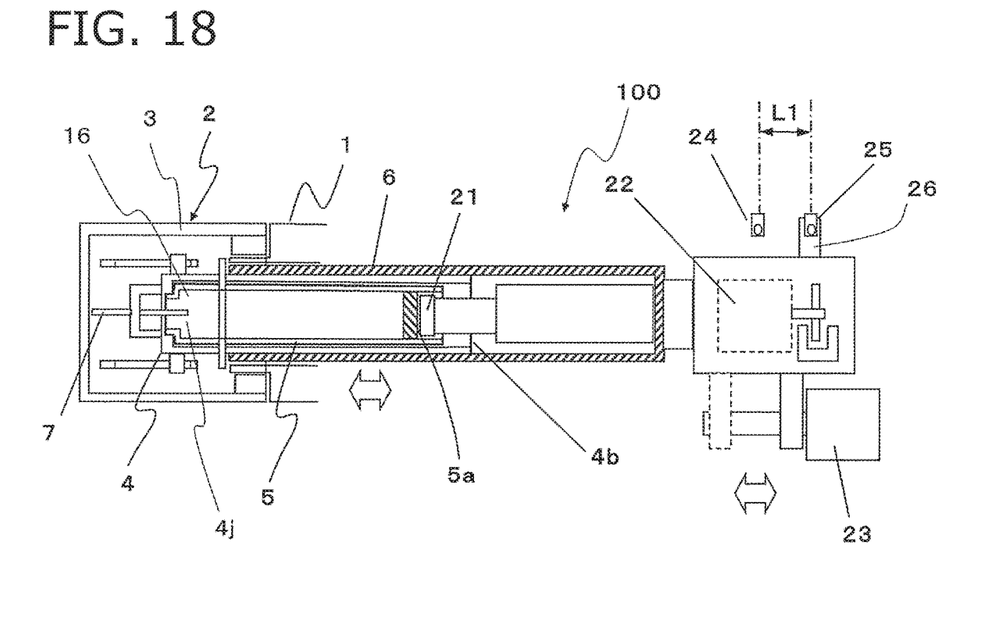
FIG. 18 is a simplified diagram of the internal configuration of the pharmaceutical injection device in FIG. 1.

As shown in FIG. 18, as in a conventional configuration, a piston 21 for pushing a pharmaceutical out of the pharmaceutical cartridge 5, a first driver 22 for driving this piston 21 back and forth with respect to the main body case 1, and a second driver 23 for inserting and withdrawing a needle by driving the inner case 6 forward and backward are provided inside the main body case 1 of the pharmaceutical injection device main body 100.

Inside the main body case 1 are provided a sensor 24 for confirming the position to which the inner case 6 has moved forward (needle insertion position), and a sensor 25 for confirming the position to which the inner case 6 has moved rearward (needle withdrawal position), when the inner case 6 is moved in the forward and backward direction by the second driver 23. The sensors 24 and 25 consist of reflective or transmissive photosensors or the like, and the position of the inner case 6 is confirmed by a shield 26, which moves along with the inner case 6, that moves to the sensors 24 and 25 to block their light. The distance L1 indicates the distance that the inner case 6 moves between the needle insertion position and the needle withdrawal position.

Figure 3:
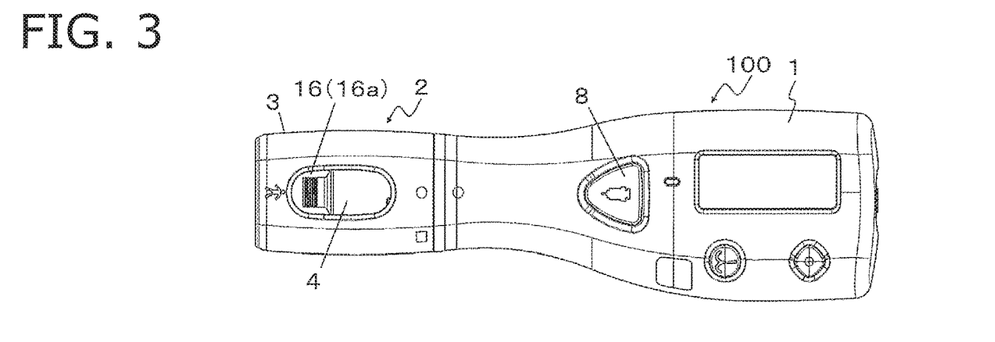
FIG. 3 is a plan view of the pharmaceutical injection device in FIG. 1.
Figure 4:
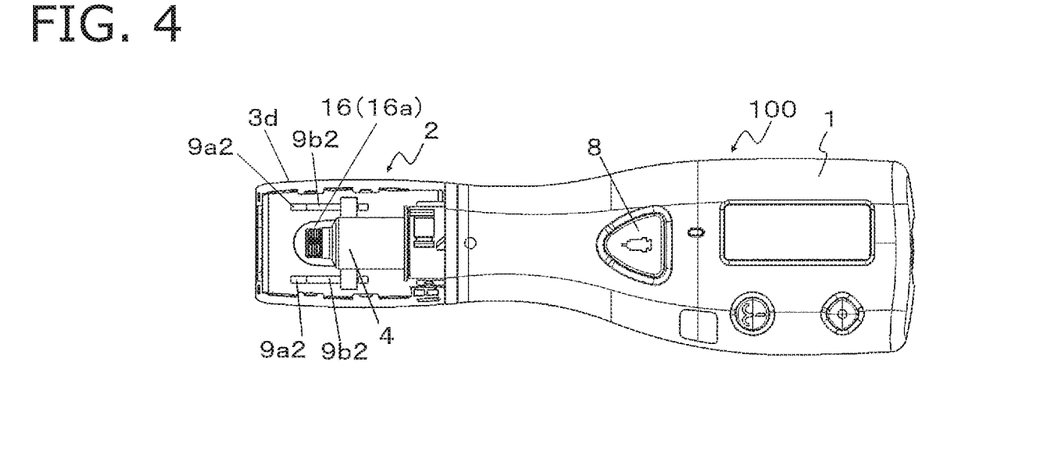
FIG. 4 is a plan view of the pharmaceutical cartridge holding unit in the pharmaceutical injection device in FIG. 1 when part of the unit has been cut away.
Figure 5:
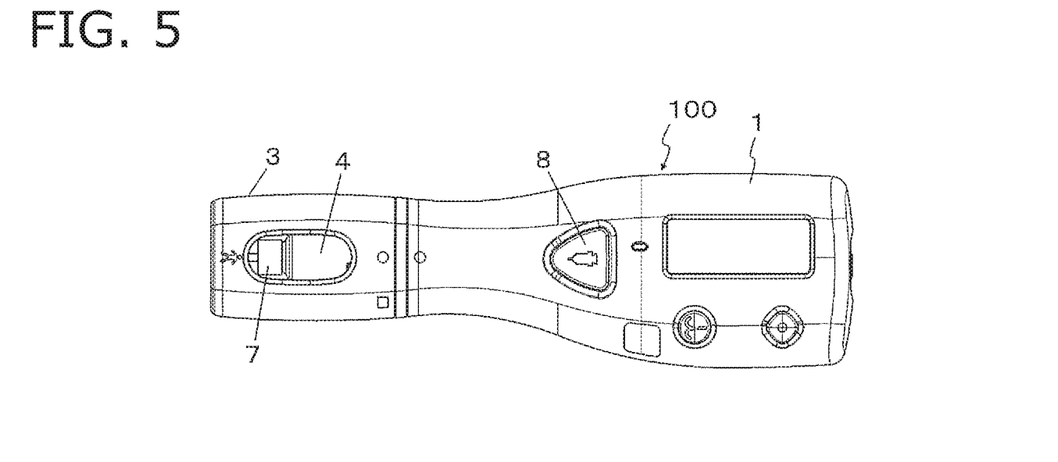
FIG. 5 is a plan view of the pharmaceutical injection device in FIG. 1.
Figure 6:
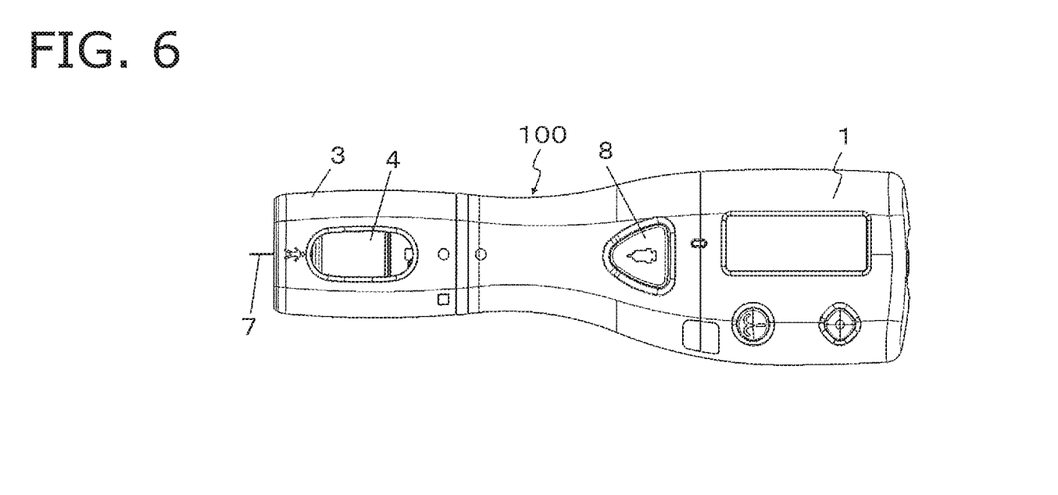
FIG. 6 is a plan view of the pharmaceutical injection device in FIG. 1.

FIGS. 3 and 4 show the state when the pharmaceutical cartridge holding unit 2 has been mounted on the distal end side of the main body case 1 in this manner. FIGS. 5 and 6 show the state when an injection needle 7 has been mounted to the distal end side of the cartridge cover 4.

In the state in FIG. 5, the distal end of the outer peripheral cap 3 comes into contact with the skin, and when an inject switch 8 is operated in this state, the above-mentioned second driver 23 causes the cartridge cover 4 mounted to the inner case 6 to move to the distal end side, and as a result the injection needle 7 sticks out from the distal end of the outer peripheral cap 3 as shown in FIG. 6. Consequently, inserting the needle into the skin is performed.

In this state, the piston 21 is then driven to the distal end side by the first driver 22. This causes the pharmaceutical in the pharmaceutical cartridge 5 to be injected through the injection needle 7 into the body.

After this, the piston 21 is stopped once the specified amount of pharmaceutical has been injected.

Once the piston 21 stops, the inner case 6 is then moved to the rear end side by the second driver 23. Consequently, the cartridge cover 4 also moves to the rear end side, and the injection needle 7 attached to the distal end part thereof also moves into the interior beyond the distal end of the outer peripheral cap 3. That is, withdrawing the needle from the skin is performed (the injection needle 7 is pulled out).

If, however, there is no pharmaceutical left in the pharmaceutical cartridge 5, then after needle withdrawal, the piston 21 is pulled back to the rear end side by the first driver 22 and is retracted to its home position, which is the initial position of the piston 21.

Figure 7A:
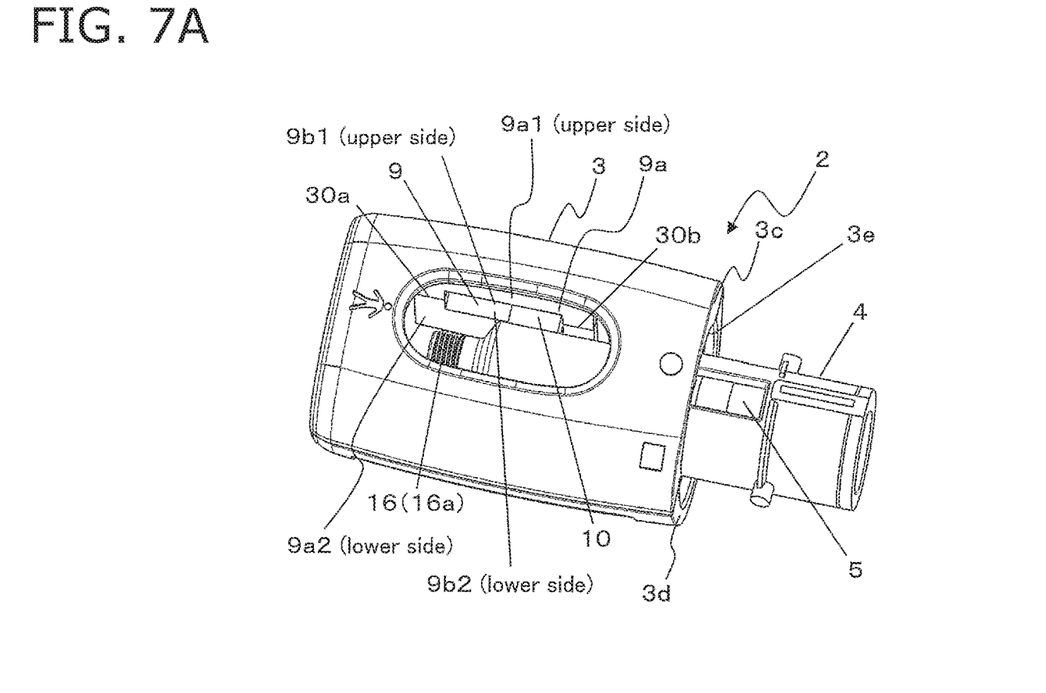
FIG. 7A is an oblique view of the pharmaceutical cartridge holding unit of the pharmaceutical injection device in FIG. 1.
Figure 7B:
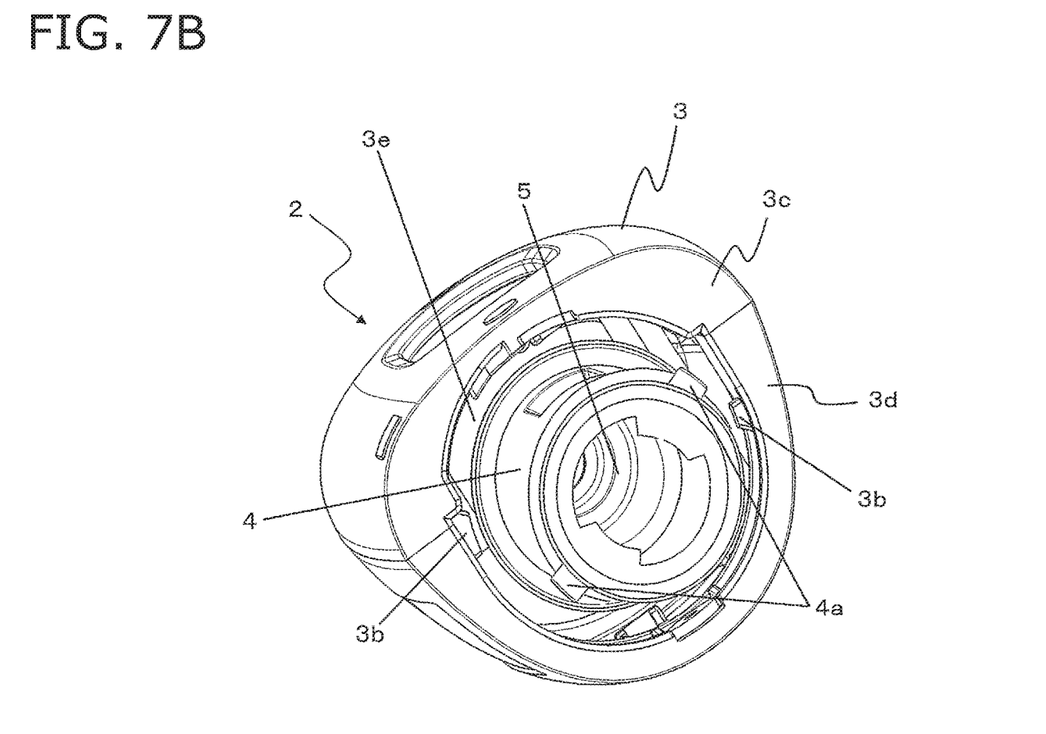
FIG. 7B is an oblique view of the pharmaceutical cartridge holding unit of the pharmaceutical injection device in FIG. 1.

After this injection of the pharmaceutical, in this embodiment, the injection needle 7 is removed from the cartridge cover 4, and then the pharmaceutical cartridge holding unit 2 is removed from the main body case 1 to create the state in FIGS. 7A and 7B, and in this state the pharmaceutical cartridge 5 is stored in a cool place, such as a refrigerator.

That is, the pharmaceutical cartridge 5 is stowed in the cartridge cover 4, and the cartridge cover 4 is stowed in the outer peripheral cap 3 to create a unit that constitutes the pharmaceutical cartridge holding unit 2, which is stored in this state in a refrigerator. The pharmaceutical cartridge holding unit 2 is configured so that at this point the cartridge cover 4 will not come loose from the outer peripheral cap 3, and the pharmaceutical cartridge 5 will not come loose from the cartridge cover 4.

4. Pharmaceutical Cartridge Holding Unit

As shown in FIGS. 7A and 7B, the pharmaceutical cartridge holding unit 2 in this embodiment comprises the outer peripheral cap 3 and the cartridge cover 4, which is disposed on the inside of the outer peripheral cap 3 and is able to move forward and backward. The outer peripheral cap 3 is substantially cylindrical, and has the distal end opening 3f on its front end side and the rear end opening 3e on its rear end side.

Figure 8:
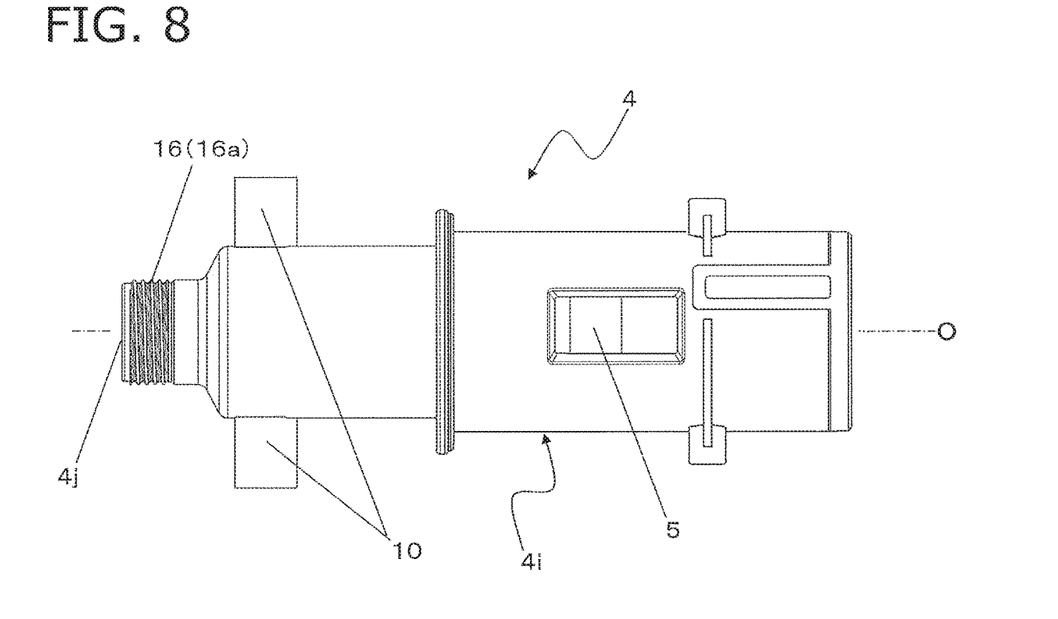
FIG. 8 is a plan view of a cartridge cover of the pharmaceutical cartridge holding unit in FIG. 7A.

FIG. 8 is a plan view of the cartridge cover 4 of the pharmaceutical cartridge holding unit 2 in this embodiment.

First, as shown in FIG. 8, flanges 10 (correspond to an example of a guided part), which are guided forward and backward by groove-like guide components 9 provided to the outer peripheral cap 3, are provided on the left and right sides around the outside of the cartridge cover 4. The flanges 10 are formed protruding outward from the side face of a cartridge cover main body 4i, and are plate shaped. The flanges 10 are disposed so that their plane follows the center axis O of the cartridge cover main body 4i. Two of the flanges 10 are provided, and these flanges 10 are disposed in symmetry with the center axis O of the cartridge cover main body 4i. The flanges 10 mate with the guide components 9 as shown in FIG. 7A.

Figure 7C:
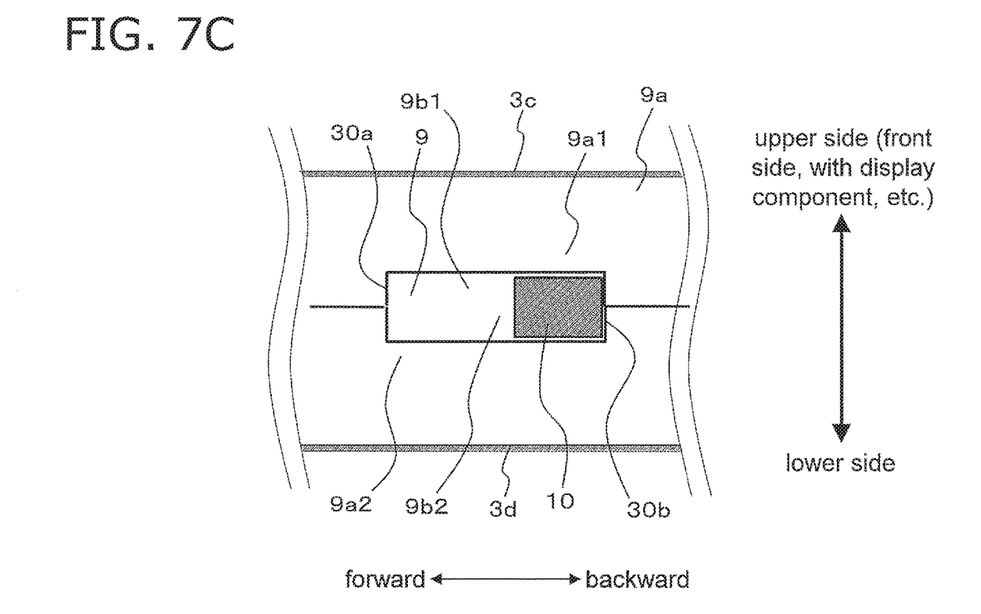
FIG. 7C is a diagram illustrating a guide component of the pharmaceutical cartridge holding unit in FIG. 7A.
Figure 7D:
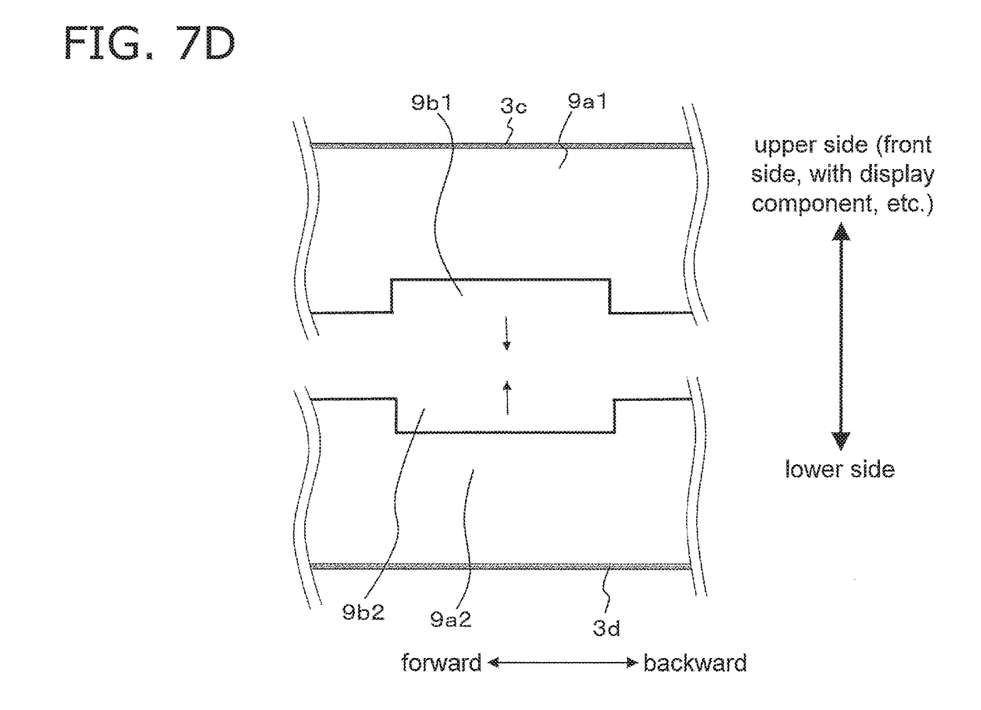
FIG. 7D is a diagram illustrating a guide component of the pharmaceutical cartridge holding unit in FIG. 7A.

FIG. 7C is a simplified diagram of guide component 9 side, from the inside of the pharmaceutical cartridge holding unit 2 in the state in FIG. 7A. FIG. 7D is an exploded view of the guide component 9 side, from the inside of the outer peripheral cap 3, in order to illustrate the configuration of the guide components 9.

As will be understood from FIG. 4 and FIGS. 7A to 7D, plate-like risers 9a are disposed on the inside of the outer peripheral cap 3. The groove-like guide components 9 are formed passing through the risers 9a, forward and backward, in the approximate center in the up and down direction of the risers 9a.

To describe this in further detail, as will be understood from FIG. 4 and FIGS. 7A to 7D, risers 9a1 and 9a2 for forming the guide components 9 are formed in the respective interiors of an upper member 3c and a lower member 3d produced by dividing the outer peripheral cap 3 into upper and lower parts. The riser 9a1 is formed facing downward from the inside of the upper member 3c, and a recess 9b1 is formed in the forward and backward direction on the lower side thereof. The riser 9a2 is formed facing upward from the inside of the lower member 3d of the outer peripheral cap 3. A recess 9b2 is formed in the forward and backward direction at the upper end thereof.

The risers 9a are formed by bringing these risers 9a1 and risers 9a2 into contact in the upper and lower direction, and the groove-like guide components 9 are formed by the recesses 9b1 and 9b2 formed in the risers 9a1 and 9a2. The configuration is such that the flanges 10 of the cartridge cover 4 are guided in the forward and backward direction within these guide components 9.

Because these flanges 10 are present inside the guide components 9, the cartridge cover 4 is prevented from coming loose from the outer peripheral cap 3.

That is, stoppers 30a and 30b are formed at the front and back of the guide components 9 by the riser 9a1 coming into contact with the riser 9a2, so the flanges 10 will not slide forward or backward past the risers 9a1 and 9a2. Therefore, this configuration prevents the cartridge cover 4 from coming loose from the outer peripheral cap 3. That is, the flange 10 is prevented from coming loose forward from the guide component 9 by the stopper 30a, and the flange 10 is prevented from coming loose rearward from the guide component 9 by the stopper 30b.

The guide components 9 and the stoppers 30a and 30b are provided on the left and right to correspond to the two flanges 10.

As shown in FIGS. 7A and 7B, in this embodiment, either the injection needle 7 has already been removed from the outer peripheral cap 3 in a state in which the pharmaceutical cartridge holding unit 2 has been removed from the main body case 1, or the pharmaceutical cartridge holding unit 2 is removed from the main body case 1 after the injection needle 7 has been mounted to a needle case 14 (see FIG. 14; discussed below).

Thus, after the pharmaceutical has been injected, in this embodiment the injection needle 7 is removed from the cartridge cover 4, and then the pharmaceutical cartridge holding unit 2 is removed from the main body case 1 to create the state in FIGS. 7A and 7B, and in this state the pharmaceutical cartridge 5 is stored in a cool place, such as a refrigerator.

That is, the pharmaceutical cartridge 5 is stowed in the cartridge cover 4, and the cartridge cover 4 is stowed in the outer peripheral cap 3 to create a unit that constitutes the pharmaceutical cartridge holding unit 2, which is stored in this state in a refrigerator. The pharmaceutical cartridge holding unit 2 is configured so that at this point the cartridge cover 4 will not come loose from the outer peripheral cap 3, and the pharmaceutical cartridge 5 will not come loose from the cartridge cover 4.

5. Holding Configuration of Pharmaceutical Cartridge 5 with Respect to Cartridge Cover 4

The mounting of the pharmaceutical cartridge 5 to the cartridge cover 4 constituting the pharmaceutical cartridge holding unit 2 will now be described through reference to FIGS. 9 to 13.

As shown in FIGS. 9 to 13, the cartridge cover 4 in this embodiment comprises the substantially cylindrical cartridge cover main body 4i and a rotary cap 11. A forward opening 4j (see FIG. 8) is formed on the front end side of the cartridge cover main body 4i, and an irregularly shaped hole 11c (see FIG. 12) is formed on the rear end side. The injection needle 7 is mounted in the forward opening 4j, and the piston 21 is inserted through the irregularly shaped hole 11c.

The rotary cap 11 comprises a tab 11a, a hinge 11d, a main body portion 11f, the irregularly shaped hole 11c, a mating rib 11e, and a rib 11b.

The tab 11a is attached so as to go into a hole 4g provided to the outer peripheral face on the rear end side of the cartridge cover main body 4i.

The hinge 11d is linked to the tab 11a. The main body portion 11f is ring shaped, and is linked to the hinge 11d. The irregularly shaped hole 11c is formed in the center of the main body portion 11f. The mating rib 11e is formed on the lower face of the main body portion 11f of the rotary cap 11. The mating rib 11e is press-fitted lightly into a rearward opening 4d in the cartridge cover main body 4i when the rotary cap 11 is closed over the rearward opening 4d of the cartridge cover main body 4i. The rib 11b is guided by a groove 4h provided to the peripheral edge of the rearward opening 4d when the rotary cap 11 is closed over the rearward opening 4d of the cartridge cover main body 4i.

Figure 9:
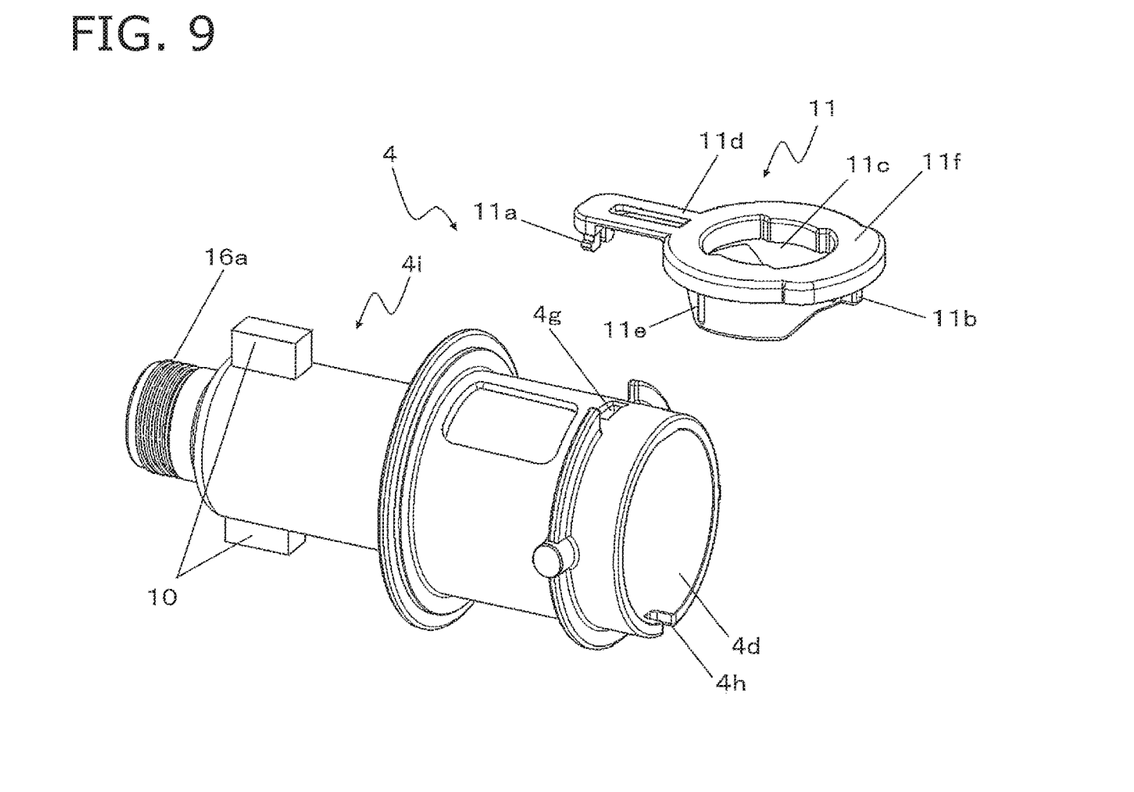
FIG. 9 is an exploded oblique view of the cartridge cover in FIG. 8.
Figure 10:
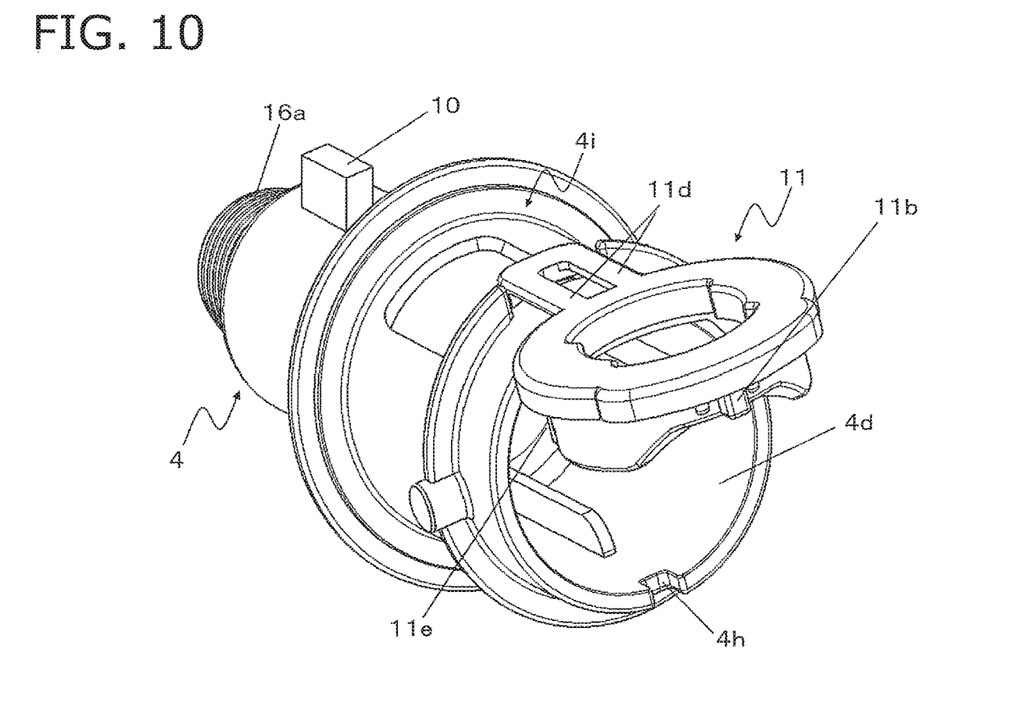
FIG. 10 is an assembled oblique view of the cartridge cover in FIG. 8.

As shown in FIGS. 9 and 10, the hinge 11d of the rotary cap 11 rotates around the tab 11a that engages with the hole 4g, with respect to the rearward opening 4d of the cartridge cover main body 4i.

Consequently, the rotary cap 11 rotates in the closing direction with respect to the rearward opening 4d of the cartridge cover main body 4i, and the rib 11b is guided by the groove 4h, so that the irregularly shaped hole 11c of the rotary cap 11 is stably fixed in a position where it is opposite the rearward opening 4d.

Since the rib 11b is thus guided by the groove 4h, even if the hinge 11d of the rotary cap 11 should be damaged and separate, the rotary cap 11 can still be positioned with respect to the rearward opening 4d.

Figure 11:
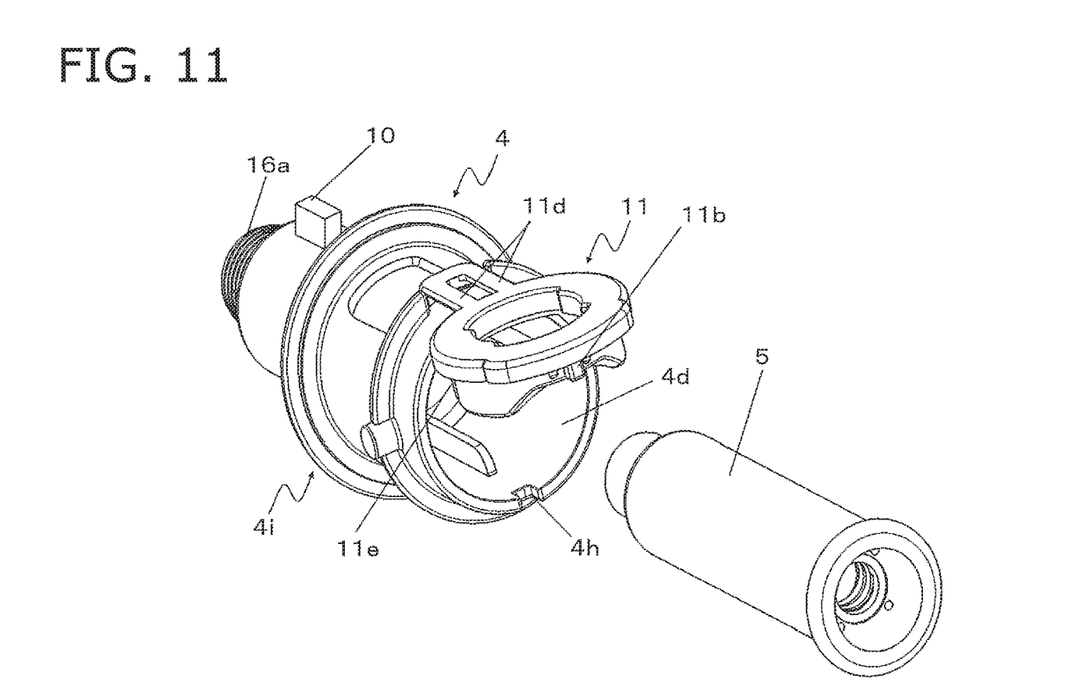
FIG. 11 is an oblique view of the state when a pharmaceutical cartridge is to be mounted to the cartridge cover in FIG. 8.
Figure 12:
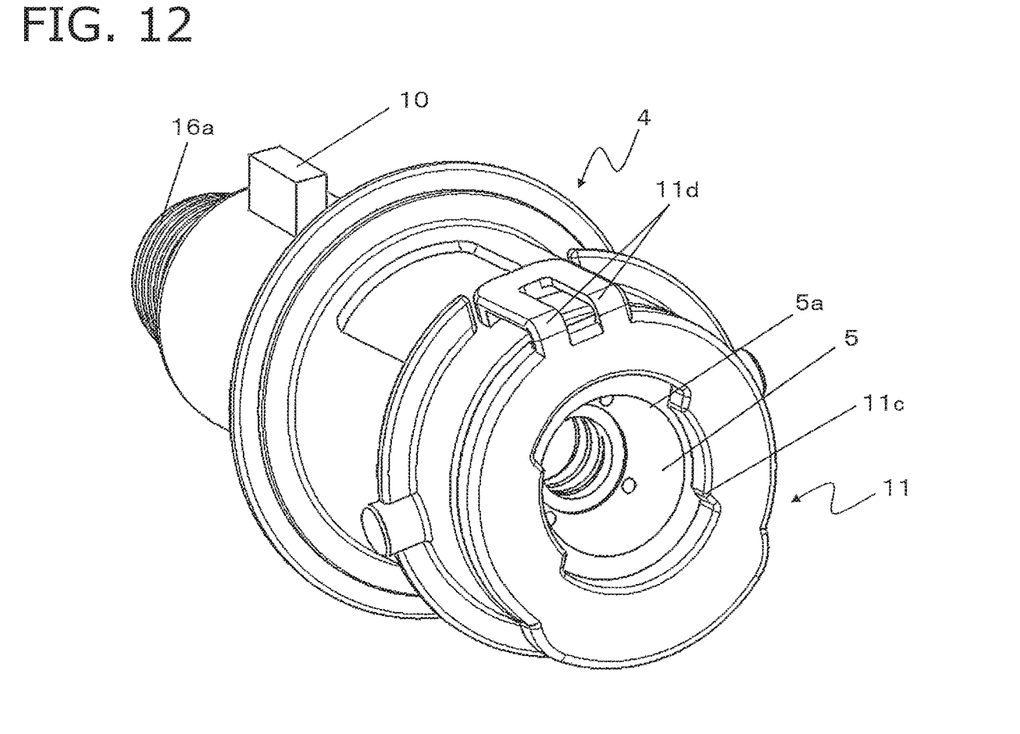
FIG. 12 is an oblique view of the state when a pharmaceutical cartridge is to be mounted to the cartridge cover in FIG. 8.

FIG. 11 shows the state when the pharmaceutical cartridge 5 is about to be inserted into the interior through the rearward opening 4d of the cartridge cover 4 to which the rotary cap 11 is attached. FIG. 12 shows the state when the pharmaceutical cartridge 5 has been inserted into the interior of the cartridge cover 4, after which the rotary cap 11 is rotated to close the rearward opening 4d.

The rear end of the pharmaceutical cartridge 5 housed in the interior of the cartridge cover 4 can be seen through the irregularly shaped hole 11c of the rotary cap 11.

As shown in FIGS. 9 to 12, the flanges 10 (correspond to an example of a guided part), which are guided in the forward and backward direction by the groove-like guide components 9 provided to the outer peripheral cap 3, are provided on the left and right around the outer periphery of the cartridge cover 4.

As discussed above, and as can be understood from FIG. 4 and FIGS. 7A to 7D, the risers 9a1 and 9a2, which are used to form the guide components 9, are provided in the respective interiors of the upper member 3c and the lower member 3d produced by dividing the outer peripheral cap 3 into upper and lower parts. These risers 9a1 and 9a2 are brought into contact from above and below, whereupon the groove-like guide components 9 are formed by the recesses 9b1 and 9b2 formed on the contact side of the risers 9a1 and 9a2, and the flanges 10 of the cartridge cover 4 are guided in the forward and backward direction within the above-mentioned guide components 9.

Also, since the flanges 10 are present inside the guide components 9, the cartridge cover 4 is prevented from coming loose from the outer peripheral cap 3.

That is, the stoppers 30a and 30b are formed at the front and back of the guide components 9 by the rise 9a1 coming in contact with 9a2, so the flanges 10 will not slide forward or backward past the risers 9a1 and 9a2. Therefore, this configuration prevents the cartridge cover 4 from coming loose from the outer peripheral cap 3.

When the pharmaceutical cartridge holding unit 2, in which the cartridge cover 4 is unified with the outer peripheral cap 3, is thus mounted to the main body case 1 of the pharmaceutical injection device, the piston 21 (see FIG. 18) of the pharmaceutical injection device passes through the irregularly shaped hole 11c and presses on a gasket 5a that is fitted in a liquid-tight fashion and so as to be able to slide on the inside of the pharmaceutical cartridge 5 housed in the cartridge cover 4, and this injects the pharmaceutical in the pharmaceutical cartridge 5 into the body.

Figure 13:
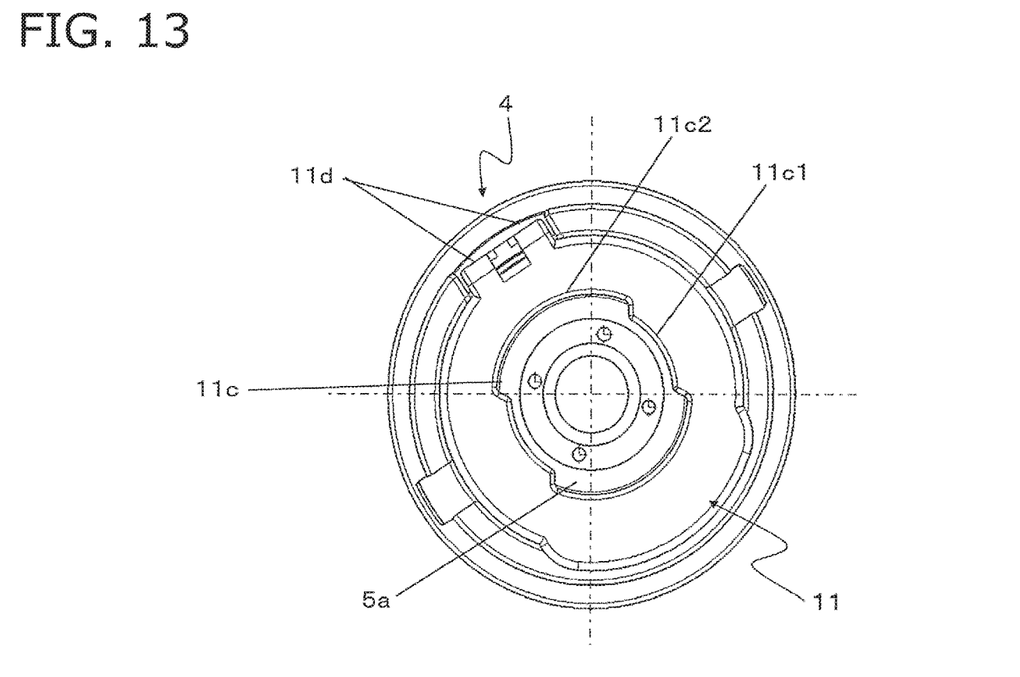
FIG. 13 shows the state in FIG. 12 as seen from the rear end.

This will be described through reference to FIG. 13. FIG. 13 is a view from the rear end of the pharmaceutical cartridge 5. That is, FIG. 13 shows the rearward opening 4d side of the cartridge cover 4 as seen from the front. As shown in FIG. 13, the gasket 5a of the pharmaceutical cartridge 5 is visible from the front through the irregularly shaped hole 11c of the rotary cap 11 fixed to the cartridge cover 4.

This irregularly shaped hole 11c has portions of different diameters, and a small diameter portion 11c1 that is smaller in diameter supports part of the rear end of the pharmaceutical cartridge 5 housed in the interior, and fixes the pharmaceutical cartridge 5.

The large diameter portion 11c2 of the irregularly shaped hole 11c (which has a larger diameter) is configured to accept the distal end portion of a detector lever (not shown) that detects the pharmaceutical cartridge 5.

6. Injection Needle 7 and Needle Unit 12 Including Same

Next, the injection needle 7 used in injecting the pharmaceutical contained in the pharmaceutical cartridge 5 into the body with the pharmaceutical injection device, and a needle unit 12 that includes this injection needle 7, will be described through reference to FIGS. 14 and 15.

Figure 14:
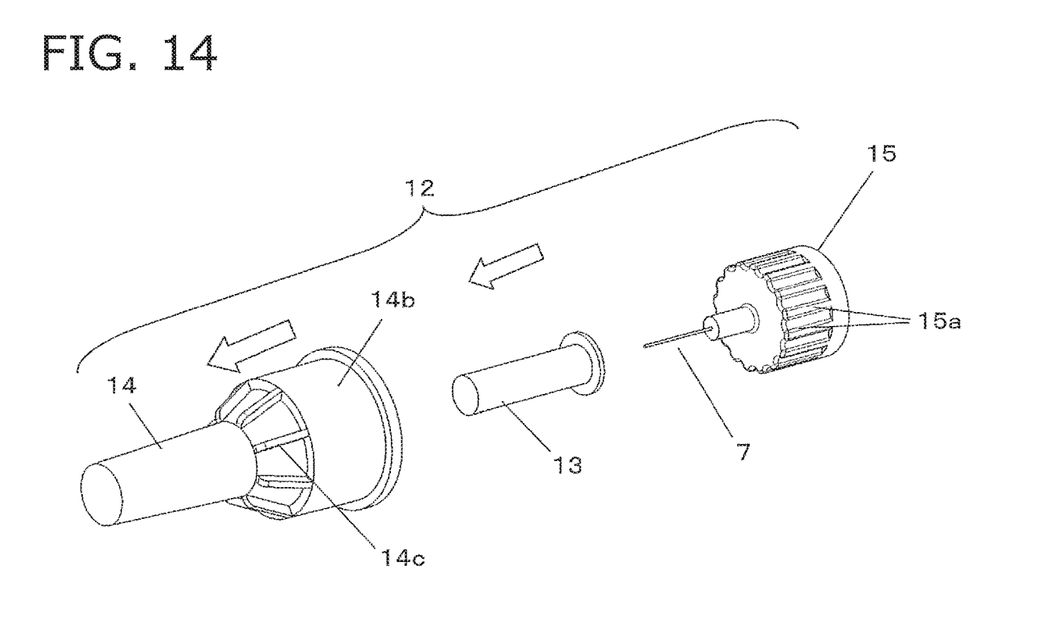
FIG. 14 is an exploded oblique view of a needle unit of the pharmaceutical injection device in FIG. 1.
Figure 15:
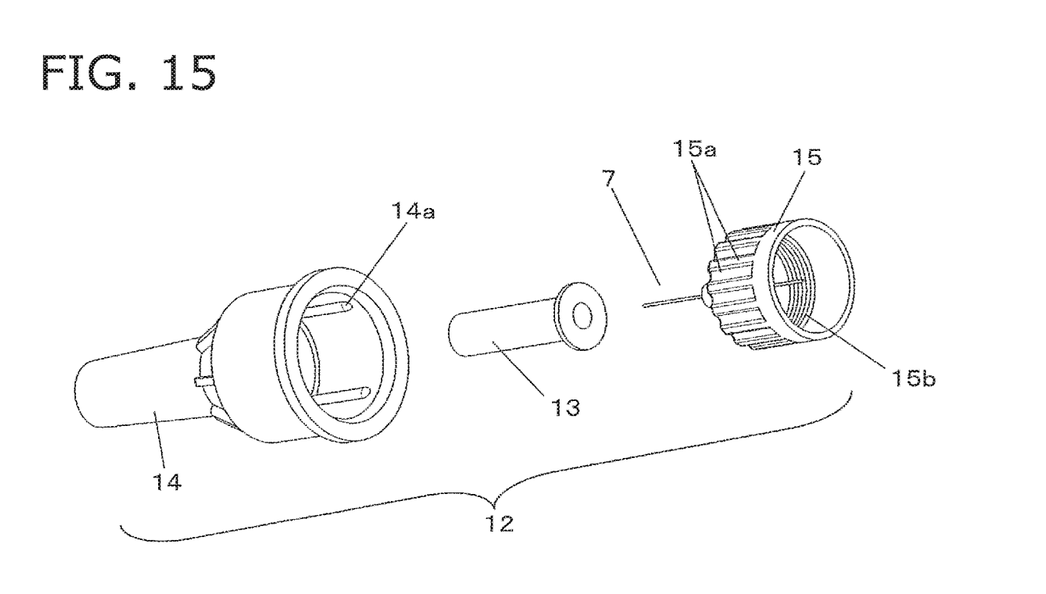
FIG. 15 is an exploded oblique view of the needle unit of the pharmaceutical injection device in FIG. 1.

FIGS. 14 and 15 are exploded oblique views of the needle unit 12. As shown in FIGS. 14 and 15, the needle unit 12 is made up of the injection needle 7, a needle cap 13 that covers the needle tip portion, and the needle case 14 that covers the injection needle 7 and the needle cap 13.

A needle base 15, which is the main body portion of the injection needle 7, has a cylindrical shape, an uneven part 15a is formed unevenly on the outer peripheral face of the needle base 15, and this part engages with protrusions 14a provided on the inner peripheral part of the needle case 14.

This is provided to allow operation while the needle case 14 is still covering the injection needle 7 while the injection needle 7 is being attached or removed, and this affords safe operation without the user having to grasp the injection needle directly.

The needle case 14 has on one side a large diameter part 14b, and a knurled part 14c is provided to the portion linked to this large diameter part 14b.

This affords a size that is easier for the user to grasp while operating the needle case 14 with his fingers, and the knurled part 14c causes a good grip that makes operation easier.

Female threads 15b are provided on the inner peripheral side of the needle base 15 of the injection needle 7. These female threads 15b mesh with male threads 16a of a needle mounting component 16 attached to the distal end part of the cartridge cover main body 4i, which attaches the injection needle 7 to the needle mounting component 16 (see FIG. 4, FIG. 5, etc.).

When the injection needle 7 is removed and discarded after injection of the pharmaceutical, the needle cap 13 is not used, and the injection needle 7 is covered directly by the needle case 14.

7. Pharmaceutical Injection Method

The method for mounting the pharmaceutical cartridge holding unit 2 to the main body case 1 of the pharmaceutical injection device, and actually injecting the pharmaceutical will now be described.

First, the pharmaceutical cartridge holding unit 2 in the state prior to being mounted to the main body case 1 will be described. As shown in FIG. 11, the pharmaceutical cartridge 5 is housed inside the cartridge cover 4. When the rotary cap 11 is then closed, the rib 11b of the rotary cap 11 goes into the groove 4h of the cartridge cover 4, and the pharmaceutical cartridge 5 is held in the interior of the cartridge cover 4.

Also, the cartridge cover 4 holding the pharmaceutical cartridge 5 is mounted in the interior of the outer peripheral cap 3, and this constitutes the pharmaceutical cartridge holding unit 2.

As shown in FIGS. 4, 7A, 7C, 7D, 16, and 17, at this point the flanges 10 provided around the outside of the cartridge cover 4 are engaged with the groove-like guide components 9 of the outer peripheral cap 3, which restricts movement of the cartridge cover 4 on the same side as the needle mounting component 16 (the front side) and on the opposite side to within a specific range. This prevents the cartridge cover 4 from coming loose from the outer peripheral cap 3 constituting the pharmaceutical cartridge holding unit 2.

Therefore, because the pharmaceutical cartridge 5 is held by the cartridge cover 4, and the cartridge cover 4 is restricted from coming loose from the outer peripheral cap 3, this prevents the pharmaceutical cartridge 5 from coming loose from or falling out of the pharmaceutical cartridge holding unit 2.

Thus, the pharmaceutical cartridge holding unit 2 can be stored in a cool place such as a refrigerator, and can also be taken out of the refrigerator and mounted to the main body case 1 of the pharmaceutical injection device, in a state in which this pharmaceutical cartridge 5 is held, which is extremely convenient for the user.

The pharmaceutical cartridge holding unit 2 in a state in which the pharmaceutical cartridge 5 has been mounted is then mounted to the main body case 1 as shown in FIGS. 1 and 2.

At this point, the cartridge cover 4 engages with the inner case 6 of the main body case 1. The piston 21 (see FIG. 18) that moves inside the inner case 6 is disposed at a location that is opposite the rear end of the pharmaceutical cartridge 5 housed in the interior of the cartridge cover 4, passing through the rearward opening of the pharmaceutical cartridge holding unit 2 (the portion corresponding to the rearward opening 4d of the cartridge cover main body 4i (an example of a piston insertion component); see FIG. 9).

That is, the piston 21 is disposed at a location opposite the rearward opening 4d (an example of a piston insertion component) of the cartridge cover 4.

Therefore, the pharmaceutical in the pharmaceutical cartridge 5 can be injected into the body by the drive of this piston 21.

Thus, it is possible to prepare for pharmaceutical injection by simply mounting to the main body case 1 of the pharmaceutical injection device in a state in which the pharmaceutical cartridge 5 is still mounted to the pharmaceutical cartridge holding unit 2, and after the injection, the pharmaceutical cartridge holding unit 2 to which the pharmaceutical cartridge 5 is still mounted can be stored in a cool place such as a refrigerator, so the process is completed reliably and easily.

8. Pharmaceutical Cartridge Holding Unit 2 when Injection Needle 7 is Mounted

The features of the pharmaceutical cartridge holding unit 2 when the injection needle 7 has been mounted will now be described through reference to FIGS. 7C, 7D, 16, and 17.

The pharmaceutical cartridge holding unit 2 in this embodiment is developed for use in a pharmaceutical injection device, naturally during pharmaceutical injection, the injection needle 7 is used to inject the pharmaceutical into the body.

Figure 16:
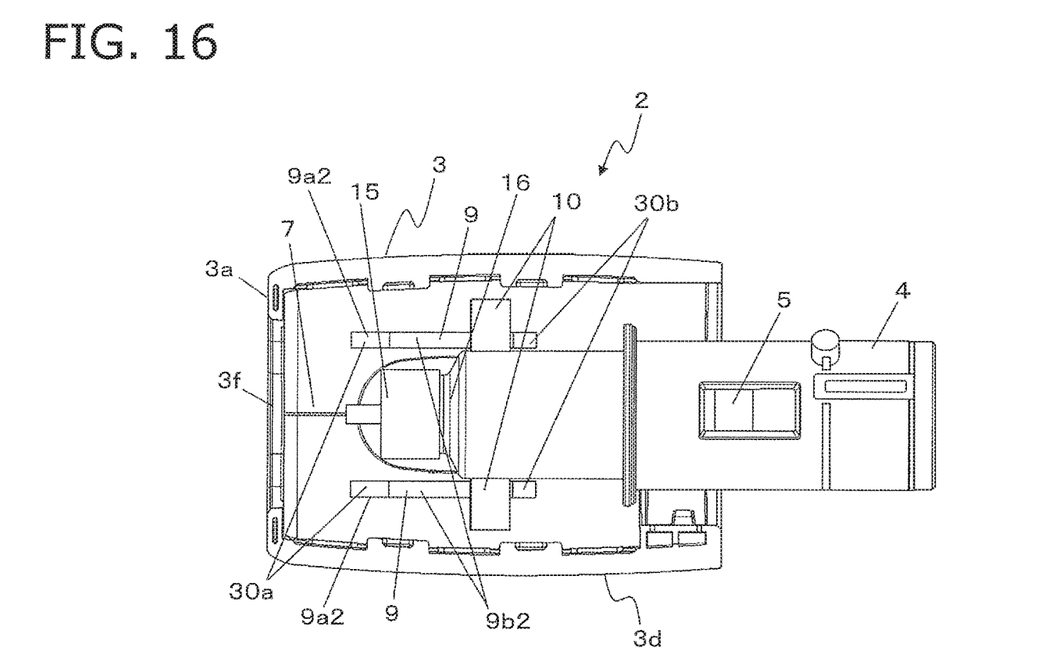
FIG. 16 is a cross section showing the state when an injection needle has been mounted to the pharmaceutical cartridge holding unit in FIG. 7A.
Figure 17:
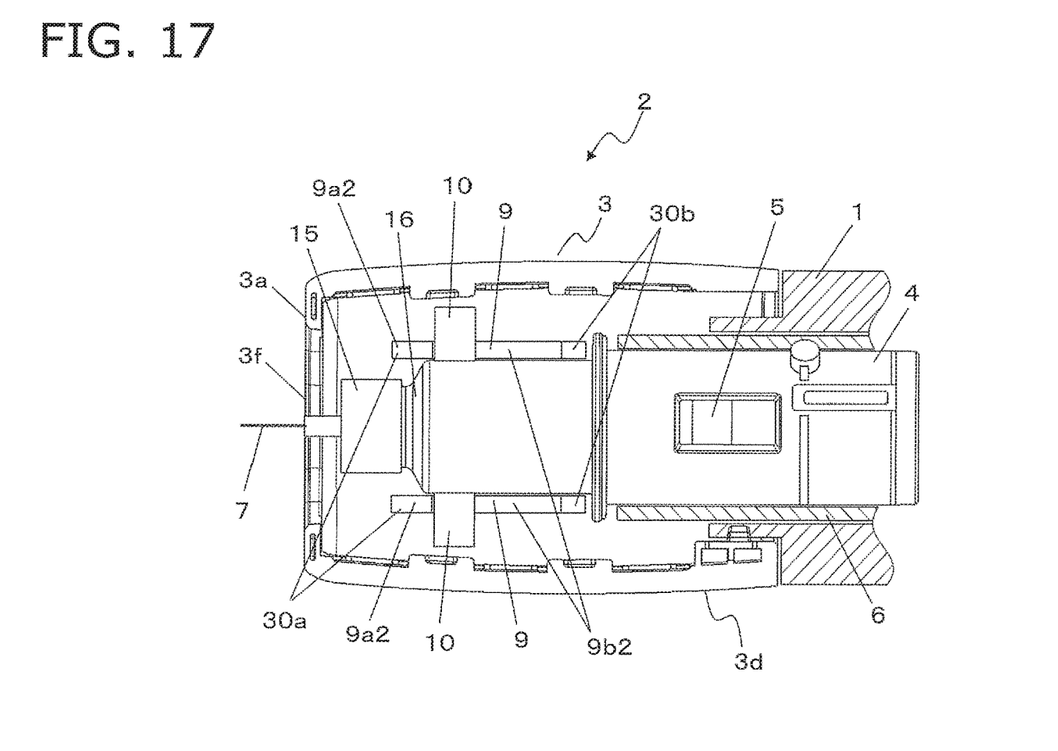
FIG. 17 is a cross section showing the state when the pharmaceutical cartridge holding unit in FIG. 7A, to which an injection needle has been mounted, is disposed at the needle insertion position.

FIGS. 16 and 17 show the pharmaceutical cartridge holding unit 2 in a state in which the injection needle 7 has been mounted to the needle mounting component 16 provided at the distal end of the cartridge cover 4. FIG. 16 shows the state when the pharmaceutical cartridge holding unit 2 is removed from the main body case 1 of the pharmaceutical injection device. FIG. 17 shows the state when the pharmaceutical cartridge holding unit 2 is mounted to the main body case 1. In FIGS. 16 and 17, only the lower member 3*d* is shown for the outer peripheral cap 3, and the upper member 3*c* has been removed.

Figure 19:
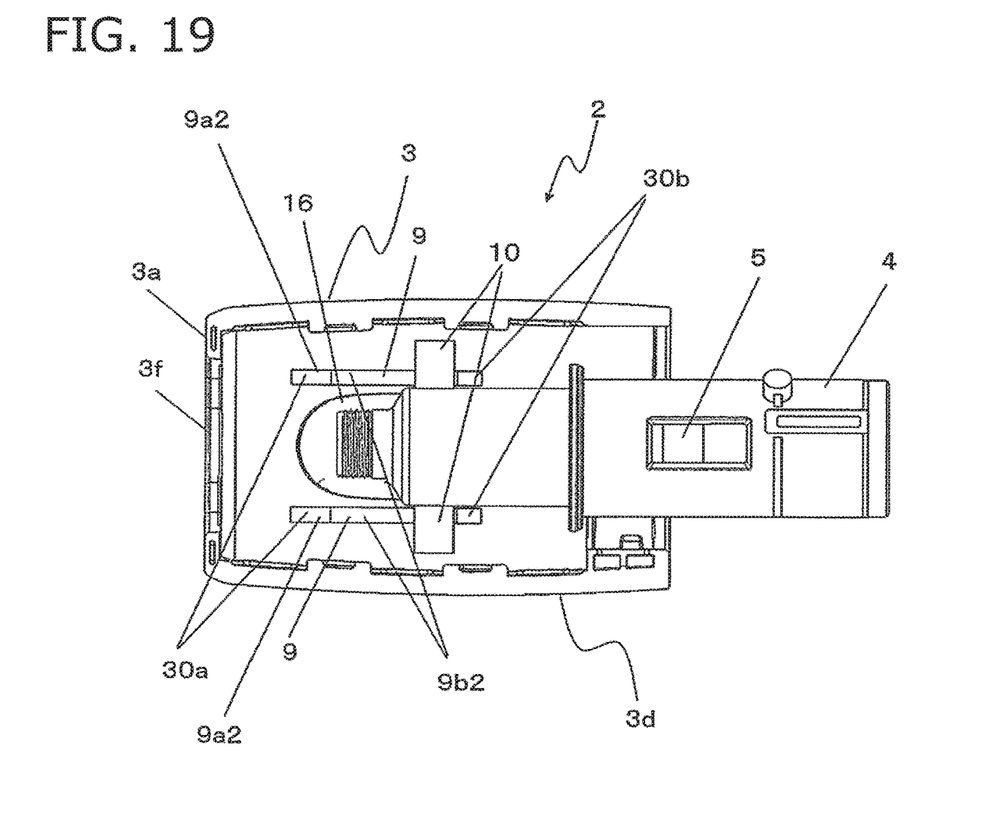
FIG. 19 is a cross section of the state when the needle is withdrawn from the pharmaceutical cartridge holding unit in FIG. 16.

FIG. 19 shows the state when the injection needle 7 has been removed from FIG. 16.

First, the pharmaceutical cartridge holding unit 2 in a state of having been removed from the main body case 1 of the pharmaceutical injection device will be described through reference to FIGS. 16 and 19. FIG. 16 shows the state when the injection needle 7 has been attached to the pharmaceutical cartridge holding unit 2, but usually the injection needle 7 is removed when removing the pharmaceutical cartridge holding unit 2 from the main body case 1, as shown in FIG. 19.

As discussed above, the pharmaceutical cartridge holding unit 2 comprises the outer peripheral cap 3 and the cartridge cover 4, and the pharmaceutical cartridge 5 is housed and held in the interior of the cartridge cover 4.

The cartridge cover 4 housing and holding the pharmaceutical cartridge 5 is held so that at least half of itself goes into the interior of the outer peripheral cap 3.

That is, the flanges 10 of the cartridge cover 4 are guided by the guide components 9 of the outer peripheral cap 3, and the cartridge cover 4 is held in a state of being able to move forward and backward. More specifically, the pharmaceutical cartridge holding unit 2 is configured such that the flanges 10 of the cartridge cover 4 stop in the recesses 9*b*1 and 9*b*2 of the guide components 9 by sandwiched between the risers 9*a*1 and 9*a*2 constituting the guide components 9 (see FIGS. 7A to 7D). As shown in FIGS. 16, 17, and 19, the two flanges 10 are guided by the two guide components 9 so that each is sandwiched between a set of risers 9*a*1 and 9*a*2.

Therefore, the cartridge cover 4 is able to slid in the range of the recesses 9*b*1 and 9*b*2 of the guide components 9 (in other words, between the stopper 30*a* and the stopper 30*b*).

In removing the pharmaceutical cartridge holding unit 2 from the main body case 1, the needle case 14 is placed over the injection needle 7 and the injection needle 7 is removed, after which the pharmaceutical cartridge holding unit 2 is removed from the main body case 1 (see FIG. 19).

The state when the pharmaceutical cartridge holding unit 2 has been mounted to the main body case 1 of the pharmaceutical injection device will now be described through reference to FIG. 17.

Here, the part discussed in relation to FIG. 16 above will not be redundantly described again.

FIG. 17 shows the state when the pharmaceutical cartridge holding unit 2 is mounted to (engaged with) the main body case 1.

Specifically, in a state in which the pharmaceutical cartridge holding unit 2 has been mounted to the main body case 1, the cartridge cover 4 to which the injection needle 7 has been mounted is made able to slide in order to allow the needle to be inserted or withdrawn. The cartridge cover 4 is connected to the inner case 6 disposed on the inside of the main body case 1, and the sliding range is restricted by the inner case 6. Therefore, the range of the recesses 9*b*1 and 9*b*2 in the forward and backward direction is preferably set to be the same as or slightly greater than the sliding range of the inner case 6.

FIG. 17 shows the needle insertion state. This needle insertion state is a state in which the flanges 10 of the cartridge cover 4 have advanced to a location where they hit the risers 9*a*1 and 9*a*2 on the distal end side of the guide components 9 (in other words, the location of contact with the stopper 30*a* on the distal end side), that is, a state in which the inner case 6 has slid in the needle insertion direction, and a state in which the injection needle 7 protrudes from the distal end-side end face 3*a* of the outer peripheral cap 3.

That is, FIG. 17 shows the state when the injection needle 7 is inserted in the skin during pharmaceutical injection, after which injection of the pharmaceutical can begin.

Figure 20:
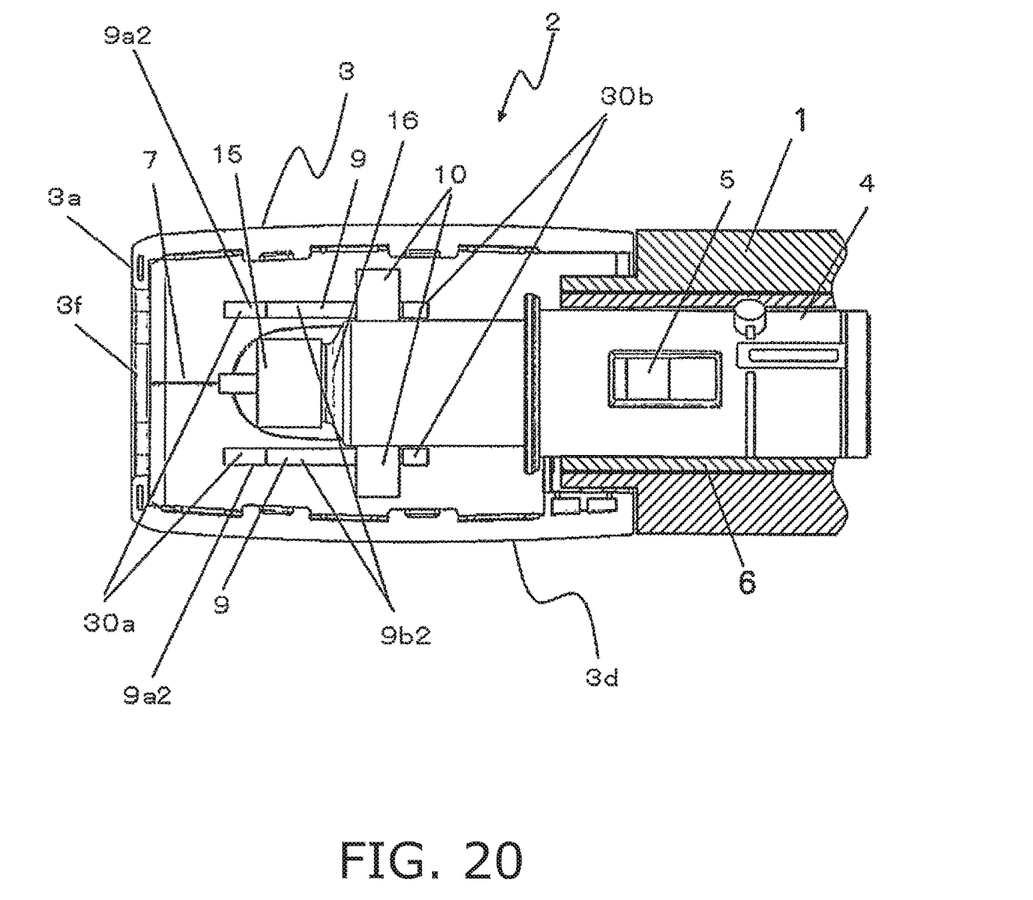
FIG. 20 is a cross section of the state when the pharmaceutical cartridge holding unit in FIG. 7A, to which an injection needle has been mounted, is disposed at the needle withdrawal position.

As shown in FIGS. 5 and 20, the needle withdrawal state is a state in which the flanges 10 of the cartridge cover 4 have receded to a location where they hit the risers 9*a*1 and 9*a*2 on the rear end side of the guide components 9 (in other words, the location of contact with the stopper 30*b* on the rear end side), that is, a state in which the inner case 6 has slid in the needle withdrawal direction. The state shown in FIGS. 16 and 19 is also a state in which the flanges 10 of the cartridge cover 4 have receded to a location where they hit the risers 9*a*1 and 9*a*2 on the rear end side of the guide components 9 (in other words, the location of contact with the stopper 30*b* on the rear end side).

At this point, the injection needle 7 is at a location where it is not exposed from the distal end-side end face 3*a* of the outer peripheral cap 3. That is, FIGS. 5 and 20 show the state when the pharmaceutical injection is finished and the injection needle 7 has been withdrawn from the skin.

As discussed above, the pharmaceutical cartridge holding unit 2 pertaining to this embodiment comprises the outer peripheral cap 3 having openings (the distal end opening 3*f* and the rear end opening 3*e*) on the distal end side and the rear end side, and the cartridge cover 4 that is held so as to be able to slide forward and backward within the outer peripheral cap 3. The outer peripheral cap 3 has the guide components 9 that slide the cartridge cover 4 forward and backward in a specific range, and the stoppers 30*a* and 30*b* that prevent the cartridge cover 4 from coming loose from the outer peripheral cap 3.

Specifically, in this embodiment, since the cartridge cover 4 is set inside the outer peripheral cap 3 and can be handled in this state, when the pharmaceutical cartridge 5 is stored in a cool place, it can be stored along with the cartridge cover 4 and the outer peripheral cap 3. Also, after storage, when the pharmaceutical is injected, these components can be mounted to the main body case 1 of the pharmaceutical injection device as the pharmaceutical cartridge holding unit 2, which makes the job extremely easy.

INDUSTRIAL APPLICABILITY

Certain implementations of the pharmaceutical cartridge holding unit of the present invention are extremely easy to use, and are expected to find use in pharmaceutical injection devices and the like that make use of a pharmaceutical that needs to be stored in a cool place such as a refrigerator every time pharmaceutical injection is performed.

The invention claimed is:

1. A pharmaceutical cartridge holding unit which holds a pharmaceutical-filled cartridge and is configured to be mounted to a pharmaceutical injection device main body, in order to mount the pharmaceutical-filled cartridge to a pharmaceutical injection device, the pharmaceutical cartridge holding unit comprising:

an outer peripheral cap having a front end side opening and a rear end side opening; and a cartridge cover on an inside of the outer peripheral cap, the cartridge cover being configured to slide forward and backward with respect to the outer peripheral cap, and the cartridge cover including a guided part protruding outward therefrom, wherein the outer peripheral cap has:
a guide component including risers with respective recesses defined therein, the guide component being configured to guide sliding of the cartridge cover forward and backward;
a stopper configured to prevent the cartridge cover from coming loose from the outer peripheral cap in a state of the pharmaceutical cartridge holding unit being separated from the pharmaceutical injection device main body; and
an engagement component that can engage with the pharmaceutical injection device main body; and
wherein the guided part is sandwiched between the risers and is configured to be guided forward and backward within the recesses.

2. The pharmaceutical cartridge holding unit according to claim 1,
wherein the engagement component is a first engagement component and the cartridge cover has:
a pharmaceutical cartridge holder that is cylindrical and holds the pharmaceutical-filled cartridge;
a piston insertion component that is on a rear end side of the pharmaceutical cartridge holder and is configured to receive a piston configured to push out the pharmaceutical inside the pharmaceutical-filled cartridge;
an injection needle mounting component on a front end side of the pharmaceutical cartridge holder; and
a second engagement component that can engage with the pharmaceutical injection device main body.

3. A pharmaceutical injection device, comprising:
the pharmaceutical cartridge holding unit according to claim 2;
a main body case having the pharmaceutical cartridge holding unit mounted to a front end side of the main body case;
an inner case that is inside the main body case and can slide with respect to the main body case;
a piston that is inside the main body case;
a first driver configured to drive the piston forward and backward with respect to the main body case; and
a second driver configured to drive the inner case forward and backward with respect to the main body case,
wherein the main body case has a first engaged part configured to engage the first engagement component of the outer peripheral cap, the first engaged part being on a front end side of the main body case, and
wherein the inner case has a second engaged part configured to engage the second engagement component which is on a rear end side of the cartridge cover, the second engaged part being on a front end side of the inner case.

4. The pharmaceutical injection device according to claim 3,
wherein the cartridge cover has a holder that removably holds the pharmaceutical-filled cartridge.

5. The pharmaceutical cartridge holding unit according to claim 1,
wherein the cartridge cover has a holder that removably holds the pharmaceutical-filled cartridge.

6. The pharmaceutical cartridge holding unit according to claim 1,
wherein the guide component is groove-shaped and defined along forward and backward directions so as to have a length that is greater than a width of the guided part in forward and backward directions, and
wherein the stopper is on a front end and a rear end of the guide component, and is configured to come into contact with the guided part to prevent the cartridge cover from coming loose from the outer peripheral cap.

* * * * *